US010596151B2

(12) United States Patent
Godtfredsen et al.

(10) Patent No.: US 10,596,151 B2
(45) Date of Patent: Mar. 24, 2020

(54) METHODS AND PHARMACEUTICAL COMPOSITIONS FOR REDUCING ARTERIAL STIFFNESS WITH A COMBINATION OF A THERAPEUTIC AGENT BLOCKING THE ANGIOTENSIN RECEPTOR AND A THERAPEUTIC AGENT INHIBITING THE NEP ENZYME

(71) Applicants: Sven Erik Godtfredsen, Chatham, NJ (US); Dion Hubert Zappe, Andover, NJ (US); Weinong Guo, Bridgewater, NJ (US); Jack Ziyu Zhang, Fortworth, TX (US)

(72) Inventors: Sven Erik Godtfredsen, Chatham, NJ (US); Dion Hubert Zappe, Andover, NJ (US); Weinong Guo, Bridgewater, NJ (US); Jack Ziyu Zhang, Fortworth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/755,733

(22) PCT Filed: Aug. 24, 2016

(86) PCT No.: PCT/IB2016/055045
§ 371 (c)(1),
(2) Date: Feb. 27, 2018

(87) PCT Pub. No.: WO2017/037577
PCT Pub. Date: Mar. 9, 2017

(65) Prior Publication Data
US 2019/0022063 A1    Jan. 24, 2019

Related U.S. Application Data

(60) Provisional application No. 62/211,075, filed on Aug. 28, 2015.

(51) Int. Cl.
| *A61K 31/41* | (2006.01) |
| *A61P 9/12* | (2006.01) |
| *A61P 9/04* | (2006.01) |
| *A61P 9/10* | (2006.01) |
| *A61P 25/28* | (2006.01) |
| *A61K 31/437* | (2006.01) |
| *A61K 31/225* | (2006.01) |
| *A61K 31/216* | (2006.01) |

(52) U.S. Cl.
CPC ............ *A61K 31/41* (2013.01); *A61K 31/225* (2013.01); *A61K 31/437* (2013.01); *A61P 9/04* (2018.01); *A61P 9/10* (2018.01); *A61P 9/12* (2018.01); *A61P 25/28* (2018.01); *A61K 31/216* (2013.01); *A61K 2300/00* (2013.01)

(58) Field of Classification Search
CPC .. A61K 31/41; A61K 2300/00; A61K 31/216; A61P 9/10; A61P 25/28; A61P 9/04; A61P 9/12
See application file for complete search history.

(56) References Cited

FOREIGN PATENT DOCUMENTS

| WO | 2003/059345 A1 | 7/2003 |
| WO | 2007/056546 A1 | 5/2007 |
| WO | 2009/061713 A1 | 5/2009 |
| WO | 2014/029848 A1 | 2/2014 |

OTHER PUBLICATIONS

Ruilope et al., "Blood-pressure reduction with LCZ696, a novel dual-acting inhibitor of the angiotensin II receptor and neprilysin: a randomised, double-blind, placebo-controlled, active comparator study", The Lancet, vol. 375, No. 9722, Apr. 10, 2010, pp. 1255-1266.
Williams et al., "Rationale and study design of the Prospective comparison of Angiotensin Receptor neprilysin inhibitor with Angiotensin receptor blocker Measuring arterial stiffness in the elderly (PARAMETER) study", BMJ Open, vol . 4, No. 2, Feb. 1, 2014, pp. e004254.
Solomon et al.: "The angiotensin receptor neprilysin inhibitor LCZ696 in heart failure with preserved ejection fraction: a phase 2 double-blind randomised controlled trial", The Lancet (www.thelancet.com), Aug. 2012; vol. 380 (No. 9851), pp. 1387-1395.
Mancia et al.: "Diagnostic and therapeutic problems of isolated systolic hypertension", Journal of Hypertension, Jan. 2015, vol. 33, No. 1, pp. 33-43.
Izzo et al.: "Comparative efficacy of valsartan and LCZ696, an angiotensin receptor neprilysin inhibitor (ARNI), in hypertensive individuals over age 65", Journal of Hypertension, (2014); vol. 32, e-supplement 1, e81-e82, 6D.06.
Izzo et al.: "Efficacy of LCZ696, an angiotensin receptor-neprilysin inhibitor (ARNI) in patients with stage 1-2 systolic hypertension", Journal of the American Society of Hypertension, (2014), 8(4S), e30.
Ruilope et al.: "Efficacy of LCZ696, an angiotensin receptor neprilysin inhibitor (ARNI), in obese and overweight subjects with hypertension", European Heart Journal, ( 2014 ), 35 (Abstract Supplement ), 65.
Izzo et al.: "Age and the efficacy of LCZ696, an angiotensin receptor-neprilysin inhibitor (ARNI), compared to valsartan in patients with systolic hypertension", Journal of the American Society of Hypertension, 8(4S) (2014) e27-e28.

(Continued)

*Primary Examiner* — Sarah Pihonak
*Assistant Examiner* — Jason Deck
(74) *Attorney, Agent, or Firm* — Judith D. Kuntz

(57) ABSTRACT

The present invention relates to methods and pharmaceutical compositions for reducing arterial stiffness in a human patient showing at least one symptom selected from increased pulse wave velocity (PWV) and increased pulse pressure (PP) comprising administration to said patient of a therapeutically effective amount or a prophylactically effective amount of a combination of a therapeutic agent blocking the angiotensin receptor and a therapeutic agent inhibiting the NEP enzyme, in particular of a combination of sacubitril or a pharmaceutically acceptable salt thereof and valsartan or a pharmaceutically acceptable salt thereof in a 1:1 molar ratio.

20 Claims, 5 Drawing Sheets

(56) References Cited

OTHER PUBLICATIONS

Mizuno, Toshiki, "Early Diagnosis of Dementia and Protection", Kyofu Idaisha (Journal of Kyoto Prefectural University of Medicine, 119(6):425-436. 2010.
Rinsyo Shinkeigaku, Clinical Neurology, 50:539-546. 2010.
Katsi, V., et al., "Angiotensin receptor neprilysin inhibitor LCZ696: a novel targeted therapy for arterial hypertension?" European Heart Journal—Cardiovascular Pharmacotherapy (2015) 1, 260-264.
Mitchell, G. F., et al., "Omapatrilat Reduces Pulse Pressure and Proximal Aortic Stiffness in Patients With Systolic Hypertension" Circulation, (2002),vol. 105, p. 2955-2961.
Noukousoku/Shinkinkousoku Wo Fuseguniwa (To prevent cerebral infarction/myocardial infarction),Tyuukan Houjin Nihon Rinsyounaika Ikai (Japan Physicians Association), (2006), p. 4.
Hokensi Yumichan Ga Tsutaetai Jyuu No Koto (Ten things concerning hypertension that the public healthnurse, Yumi-chan, wish to tell), Zenkoku Kenkou Hoken Kyokai (Kyokai Kenpo) Tottorisibu Kikakusoumu group (Japan Health Insurance Association, Tottori Branch, General Affairs and Planning Group), (May 2014), p. 4-5.

METHODS AND PHARMACEUTICAL COMPOSITIONS FOR REDUCING ARTERIAL STIFFNESS WITH A COMBINATION OF A THERAPEUTIC AGENT BLOCKING THE ANGIOTENSIN RECEPTOR AND A THERAPEUTIC AGENT INHIBITING THE NEP ENZYME

RELATED APPLICATIONS

This application is a national stage application, filed under 35 U.S.C. § 371, of International Application No. PCT/IB2016/055045, filed Aug. 24, 2016, which claims priority to, and the benefit of, U.S. provisional application No. 62/211,075, filed Aug. 28, 2015, the entire contents of each of which are incorporated herein by reference in their entireties.

The present invention relates to methods and pharmaceutical compositions for reducing arterial stiffness in a human patient showing at least one symptom selected from increased pulse wave velocity (PWV) and increased pulse pressure (PP) comprising administration to said patient of a therapeutically effective amount or a prophylactically effective amount of a combination of a therapeutic agent blocking the angiotensin receptor and a therapeutic agent inhibiting the NEP enzyme, in particular of a combination of sacubitril or a pharmaceutically acceptable salt thereof and valsartan or a pharmaceutically acceptable salt thereof in a 1:1 molar ratio.

BACKGROUND OF THE INVENTION

Cardiovascular Diseases

Hypertension accounts for 9.4 million cardiovascular (CV) deaths annually worldwide and is affecting more than two-thirds of people aged 65 years, an age group that is growing globally. The treatment of hypertension has been shown to reduce the risk of morbidity and mortality associated with elevated blood pressure (BP) including stroke, ischaemic heart disease, heart failure, chronic kidney disease and possibly cognitive decline. Despite the availability of multiple drug classes with different mechanisms of action, hypertension, especially systolic blood pressure (SBP), remains inadequately controlled.

The SBP usually increases from childhood throughout the life, while diastolic BP (DBP) remains relatively constant or decreases beyond 50 to 60 years of age. The changing patterns of BP throughout the life reflect different pathologies. In the young, hypertension is predominantly due to an increased DBP and mean arterial pressure (MAP), as a result of a relative increase in cardiac output and/or increased peripheral vascular resistance. On the other hand, advancing age, beyond mid-life, is associated with an increased stiffness of large elastic arteries, especially the aorta.

Arterial stiffening adversely affects the characteristic impedance of the aorta, requiring more cardiac work and raising SBP as more stroke volume is delivered during systole owing to the increased pulse wave velocity (PWV). DBP also decreases due to less elastic recoil leading to reduced flow, thus increasing pulse pressure (PP) independent of any changes in MAP. PWV been shown to be an independent predictor of CV outcomes, including mortality, myocardial infarction (MI), stroke, atrial fibrillation, cognitive decline and renal dysfunction, and more specifically aortic PWV (aPWV), a robust measure of aortic arterial stiffness, has been shown to predict the adverse CV outcomes.

Another consequence of arterial ageing and stiffening is that the amplification of SBP and PP from the aortic root to the peripheral arteries diminishes. In a healthy arterial system, central aortic systolic pressure (CASP) and PP are amplified as they move towards the periphery, such that the measured brachial systolic pressure is typically 10 to 12 mm Hg higher than the corresponding aortic root pressure. With ageing, this amplification is reduced and the measured brachial SBP and PP become closer to the corresponding aortic root pressures. Some studies have suggested that central pressures may have a closer correlation than peripheral BP with end organ damage and CV risk, such as extent of coronary atherosclerosis, carotid intima-media thickness, left ventricular (LV) hypertrophy, and left ventricular (LV) diastolic function.

These observations raise the intriguing question as to whether treatments used to lower blood pressure could differentially affect aortic relative to brachial pressures and also arterial stiffness per se. It has been demonstrated that BP-lowering drugs can have marked differential effects on central aortic pressure (CAP) and brachial BP. These effects mimic a functional anti-ageing effect in terms of their impact on wave-form morphology, and greater reduction in central pressures relative to brachial pressures. Intriguingly, the beta-blockers, a drug class which was least effective at lowering aortic pressure also appeared to be the least effective class at reducing the risk of stroke in elderly patients. This supports the concept that the more effective lowering of aortic relative to brachial pressure may be clinically important.

Despite the findings cited above, controlling SBP remains the most important unmet need in the clinical management of hypertension. The rise in SBP and PP with ageing appears to be strongly related to arterial stiffening and increased impedance to flow through a stiff aorta. This suggests that the treatments targeting aortic stiffening and reducing characteristic impedance would be effective particularly at reducing systolic pressure. Early proof of this concept came from the studies with omapatrilat, a vasopeptidase inhibitor that simultaneously inhibits neprilysin and angiotensin-converting enzyme (ACE). Neprilysin inhibition enhances natriuretic peptide (NP) levels by blocking their degradation. NP has vasodilating actions, which could reduce aortic stiffness, improve characteristic impedance and thereby reduce SBP and PP. Studies with omapatrilat show greater improvements in aortic characteristic impedance compared with enalapril, beyond the effects of BP-lowering after 12 weeks of therapy. This benefit on aortic function was also associated with impressive data on SBP and PP lowering in patients with hypertension.

Although omapatrilat was withdrawn due to safety concerns, a proof of concept was established for concomitant inhibition of neprilysin and renin-angiotensin-aldosterone system (RAAS) with the potential to be an attractive treatment strategy to improve aortic haemodynamics. Increased NP levels also promote natriuresis and reduce sympathetic tone, together with antiproliferative and antihypertrophic effects, and inhibition of aldosterone secretion. Alongside, suppression of RAAS would be complementary to neprilysin inhibition, which attenuates vasoconstriction, reduces sodium and water retention and also inhibits the development of CV hypertrophy and adverse re-modelling.

Thus, the big challenge in hypertension treatment is to reduce the SBP, and the available evidence suggests that this could be achieved by improving the haemodynamic performance of the ageing aorta.

Sacubitril and Valsartan (LCZ696)

LCZ696 is a first-in-class angiotensin receptor neprilysin inhibitor (ARNI) being developed for the treatment of cardiovascular diseases such as hypertension and/or heart failure. Ingestion of LCZ696 results in systemic exposure to sacubitril (AHU377; (2R,4S)-5-biphenyl-4-yl-4-(3-carboxy-propionylamino)-2-methyl-pentanoic acid ethyl ester, also named N-(3-carboxy-1-oxopropyl)-(4S)-(p-phenylphenylmethyl)-4-amino-2R-methylbutanoic acid ethyl ester), a neprilysin (neutral endopeptidase 24.11, NEP) inhibitor (NEPi) prodrug which is converted to the active form LBQ657 (2R,4S)-5-biphenyl-4-yl-4-(3-carboxy-propionyl amino)-2-methyl-pentanoic acid), and valsartan providing inhibition of the angiotensin II type 1 (AT1) receptor, in a 1:1 molar ratio.

It has been shown that LCZ696 at 100, 200 and 400 mg once daily, in patients with mild-to-moderate essential hypertension, resulted in greater BP reductions than corresponding doses of valsartan alone (160 and 320 mg) and was well tolerated [Ruilope L M, Dukat A, Bohm M, et al. Lancet 2010; 375: 1255-66]. LCZ696 compared with valsartan was effective especially at reducing brachial SBP and PP. Furthermore, in patients with heart failure with preserved ejection fraction, LCZ696 has been shown to reduce N-terminal-pro B-type natriuretic peptide (NT-proBNP), a biomarker of left ventricular (LV) wall stress, to a greater extent than valsartan alone at 12 weeks and was well tolerated [Solomon S D, Zile M, Pieske B, et al. Lancet 2012; 380: 1387-95].

The compounds and pharmaceutical compositions disclosed herein include combinations of sacubitril and valsartan which compounds or pharmaceutical compositions thereof have been previously disclosed in WO 2003/059345, WO 2007/056546, WO 2009/061713, and WO 2014/029848, which are herein incorporated by reference.

Need

Overall there remains a great need to improve the haemodynamic performance of the ageing aorta and to improve, i.e. to reduce, arterial stiffness and pulse wave velocity (PWV), and thereby reducing the risk of cardiovascular events and to improve CV outcomes, reducing the risk of cognitive decline and provide a cognitive benefit, respectively, and/or reducing the risk of a cerebrovascular event.

SUMMARY OF THE INVENTION

The Prospective comparison of Angiotensin Receptor neprilysin inhibitor with Angiotensin receptor blocker MEasuring arterial sTiffness in the eldERly (PARAMETER) study was designed to compare the effect of LCZ696 with olmesartan, an ARB, on CASP, other measures of central aortic haemodynamics and arterial stiffness, and ambulatory blood pressures in elderly patients with an elevated brachial SBP and a widened PP. The widened PP was chosen as an entry criteria as being indicative of aortic stiffening and advanced aortic ageing. The objective was to determine whether the ARNI LCZ696 can reverse some of the effects of arterial ageing in elderly patients with systolic hypertension, and thereby improve aortic pressures and haemodynamics.

Surprisingly, the study showed that the ability of LCZ696 to reduce central BP and PP, more effectively than an ARB, in high-risk older patients with systolic hypertension and an increased pulse pressure. In particular, in those patients with the stiffest arteries, the LCZ696 regimen also tended to reduce PWV to a greater extent than an ARB. These results suggest that LCZ696 provides beneficial effects on central aortic hemodynamics and function, that could provide a therapeutic advantage beyond those observed with RAS blockade alone.

Accordingly, the present disclosure is in a first aspect directed to a method of reducing arterial stiffness in a human patient showing at least one symptom selected from increased pulse wave velocity (PWV) and increased pulse pressure (PP) comprising administering to said patient a therapeutically effective amount or a prophylactically effective amount of a combination of a therapeutic agent blocking the angiotensin receptor and a therapeutic agent inhibiting the NEP enzyme. In particular, the method is for treating, preventing or reducing the risk of experiencing a disorder or disease selected from cognitive impairment, a cardiovascular event, a cerebrovascular event and combinations thereof.

Such combination of a therapeutic agent blocking the angiotensin receptor and a therapeutic agent inhibiting the NEP enzyme is for example a pharmaceutical composition comprising a therapeutically effective amount, or a prophylactically effective amount, of an Angiotensin Receptor Neprilysin inhibitor (ARNi) as defined herein or a combination of the Angiotensin Receptor Blocker (ARB) valsartan with the Neutral Endopeptidase inhibitor (NEPi) sacubitril in a 1:1 molar ratio, as defined herein.

Said pharmaceutical composition comprises a therapeutically effective amount or a prophylactically effective amount of a combination of a 1:1 molar ratio of
  (i) valsartan or a pharmaceutically acceptable salt thereof; and
  (ii) sacubitril or a pharmaceutically acceptable salt thereof.

In one embodiment, said combination is provided in the form of the compound of the formula (I)

$$[(A_1)(A_2)](Na^+)_y \cdot xH_2O \qquad (I)$$

wherein
  $A_1$ is valsartan in the anionic form;
  $A_2$ is sacubitril in the anionic form;
  $Na^+$ is a sodium ion;
  y is 1 to 3; and
  x is 0 to 3.

In one embodiment thereof, the compound of formula (I) is trisodium [3-(1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

In one embodiment, the pharmaceutical composition comprises in addition one or more pharmaceutically acceptable carriers.

In a second aspect, the present invention is directed to the use of the pharmaceutical composition as defined above for the manufacture of a medicament for reducing arterial stiffness in a human patient showing at least one symptom selected from increased pulse wave velocity (PWV) and increased pulse pressure (PP).

In a third aspect, the present invention is directed to a pharmaceutical composition as defined above for use in reducing arterial stiffness in a human patient showing at least one symptom selected from increased pulse wave velocity (PWV) and increased pulse pressure (PP).

In a fourth aspect, the present invention is directed to the use of a pharmaceutical composition as defined above for reducing arterial stiffness in a human patient showing at least one symptom selected from increased pulse wave velocity (PWV) and increased pulse pressure (PP).

Further features and advantages of the disclosure will become apparent from the following detailed description of the invention.

DEFINITIONS

Figure 1:
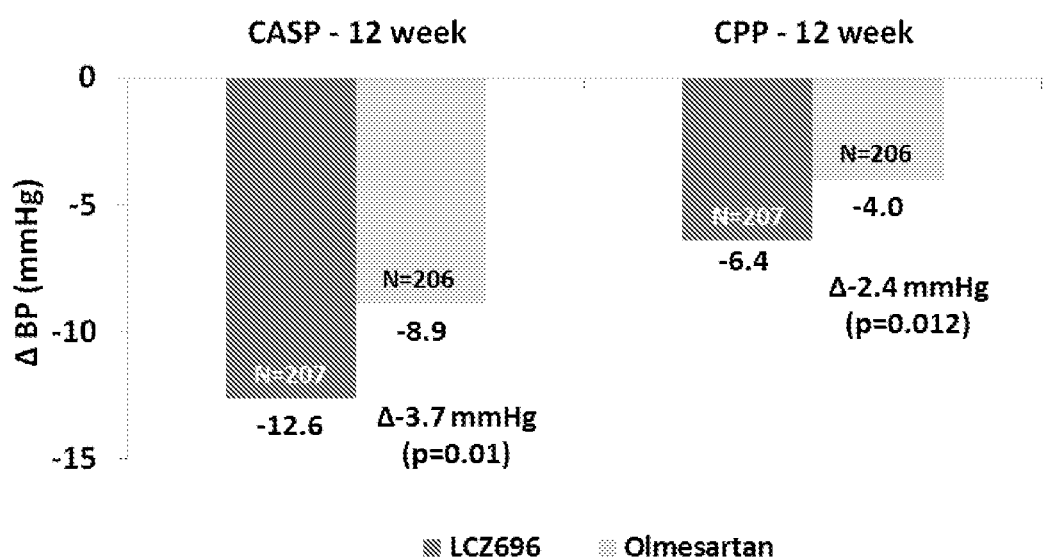
FIG. 1: Primary and key secondary outcomes: Change from baseline in mean CASP and CPP at Week 12. Abbreviations: BP, blood pressure; CASP, central aortic systolic pressure; CPP, central pulse pressure

Throughout this specification and in the claims that follow, the following terms are defined with the following meanings, unless explicitly stated otherwise.

The term "prevention" refers to prophylactic administration to a healthy subject to prevent the development of the conditions mentioned herein. Moreover, the term "prevention" means prophylactic administration to patients being in a pre-stage of the conditions to be treated.

The term "treatment" is understood the management and care of a patient for the purpose of combating the disease, condition or disorder.

The term "therapeutically effective amount" refers to an amount of a drug or a therapeutic agent that will elicit the desired biological and/or medical response of a tissue, system or an animal (including man) that is being sought by a researcher or clinician.

The terms "patient" include, but are not limited to, humans, dogs, cats, horses, pigs, cows, monkeys, rabbits and mice. The preferred patients are humans.

The terms "administration of" and or "administering a" compound should be understood to mean providing a compound of the invention or a pharmaceutically acceptable salt or ester thereof, or a pro-drug thereof to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of a disease characterized and/or manifested by atrial enlargement and/or remodeling.

As used herein, the term "about" refers to +/−20%, +/−10%, or +/−5% of a value.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

In one embodiment of the present invention, the term "sacubitril and valsartan in a 1:1 molar ratio" refers to an Angiotensin Receptor Neprilysin inhibitor (ARNi) which is a combination comprising a therapeutically effective amount of a 1:1 molar ratio of (i) valsartan or a pharmaceutically acceptable salt thereof; and (ii) sacubitril or a pharmaceutically acceptable salt thereof, and in particular trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

In addition, the term "the combination of a therapeutic agent blocking the angiotensin receptor and a therapeutic agent inhibiting the NEP enzyme comprises sacubitril and valsartan in a 1:1 molar ratio" can also refer to alternative complexes or compounds comprising valsartan and sacubitril and linking them together via non-covalent or covalent bonding, optionally via a linker.

The term "Pulse Wave Velocity" (PWV) is a measure of arterial stiffness. Pulse wave velocity (PWV) is a simple measure of the time taken by the pressure wave to travel over a specific distance. By virtue of its intrinsic relation to the mechanical properties of the artery by the Moens-Kortweg formula (PWV=$\sqrt{(Eh/2)R\rho}$; where E is the Young's Modulus of the arterial wall, h the wall thickness, R the end-diastolic radius and p is the density of blood), and buoyed a number of longitudinal studies that reported on the independent predictive value of PWV measurement for cardiovascular events and mortality in various populations, PWV is now widely accepted as the 'gold standard' measure of arterial stiffness.

In the context of the present invention PWV is measured as aortic PWV=aPWV. One system to measure aPWV is the SphygmoCor X-CEL system which measures the carotid-femoral aPWV, as the speed of the arterial pressure waveform as it travels through the descending aorta to the femoral artery, which is detected from simultaneously measured carotid and femoral arterial pulses. The carotid pulse is detected by applanation tonometry using a high-fidelity pressure transducer (Millar Instruments, Houston, Tex.), while the femoral pulse is detected using a partially inflated blood pressure cuff wrapped around the upper thigh. The distance travelled by the pulse wave is captured by making physical measurements on the body surface according to the manufacturer's recommendations. This new brachial cuff-based device with an individualised sub-diastolic cuff pressure has recently been validated against the SphygmoCor device (AtCor Medical) using the classical radial tonometry-based methodology, and provides an operator-independent method to assess systolic pressure and aortic waveform comparable with the existing validated tonometric-based methods. [Butlin M, Qasem A, Avolio A P. Estimation of central aortic pressure waveform features derived from the brachial cuff volume displacement waveform. Conf Proc IEEE Eng Med Biol Soc 2012; 2012:2591-4]

The term "pulse pressure" (PP) refers to the difference between the systolic and diastolic pressure readings. It is measured in millimeters of mercury (mmHg). It represents the force that the heart generates each time it contracts. If resting blood pressure is (systolic/diastolic).

The term CAPP refers to central aortic PP. In the context of the present invention CAPP is measured with the SphygmoCor X-CEL System (AtCor Medical, Sydney, Australia) to non-invasively derive the ascending aortic pressure waveform from the brachial waveform using a validated generalised transfer function (GTF). A properly sized BP cuff is linked to a computer and software and the CASP, CAPP, augmentation pressure, and AIx are determined from the analysis of waveform by the system software.

DETAILED DESCRIPTION OF THE INVENTION

This invention has shown based on the clinical trial described in more detail in the Example section that LCZ696 (i.e. a 1:1 molar ratio of sacubitril and valsartan) is able to reduce central BP and PP, more effectively than an ARB (e.g. olmesartan), in high-risk older patients with systolic hypertension and an increased pulse pressure. In particular in those patients with the stiffest arteries, the LCZ696 regimen also tended to reduce PWV to a greater extent than an ARB alone.

These results suggest that treatment with LCZ696 provides beneficial effects on central aortic hemodynamics and function, thereby supporting for the first time a therapeutic advantage of the treatment of an ARNI beyond those observed with RAS blockade alone.

These findings imply that LCZ696 can reverse some of the effects of arterial ageing in elderly patients with systolic hypertension, and thereby improve aortic pressures and haemodynamics.

In addition, it can be concluded that based on these observed effects and the fact that PWV, and more specifically aortic PWV (aPWV), has been shown to be an independent predictor of CV outcomes, including mortality, myocardial infarction (MI), stroke, atrial fibrillation, cognitive decline and renal dysfunction, that LCZ696 has a beneficial effect on disorders or diseases selected from cognitive impairment, a cardiovascular event, a cerebrovascular event and combinations thereof.

As a consequence LCZ696 may especially be beneficial on improving or reducing the decline of cognitive function in elderly patients with essential hypertension, thereby differentiating LCZ696 from currently available cardiovascular drugs.

Accordingly, the present invention relates to the following:

Methods of Treatment

Thus, the invention encompasses a method of reducing arterial stiffness in a human patient showing at least one symptom selected from increased pulse wave velocity (PWV) and increased pulse pressure (PP) comprising administering to said patient a therapeutically effective amount or a prophylactically effective amount of a combination of a therapeutic agent blocking the angiotensin receptor and a therapeutic agent inhibiting the NEP enzyme In one embodiment thereof, the combination of a therapeutic agent blocking the angiotensin receptor and a therapeutic agent inhibiting the NEP enzyme comprises sacubitril and valsartan in a 1:1 molar ratio In a preferred embodiment, the method is for treating, preventing or reducing the risk of experiencing a disorder or disease selected from cognitive impairment, a cardiovascular event, a cerebrovascular event and combinations thereof.

In one embodiment said cognitive impairment is selected from the group consisting of mild cognitive impairment, age related cognitive function decline, and Alzheimer's disease.

In one embodiment said cardiovascular event is selected from the group consisting of cardiovascular death, myocardial infarction (MI), atrial fibrillation, hospitalization for unstable angina, acute coronary syndrome, other non-coronary ischemic event (transient ischemic attack or limb ischemia), any revascularization procedure (coronary and non-coronary), hospitalization or prolongation of hospitalization for heart failure, and coronary revascularization procedures.

In another embodiment said cerebrovascular event is stroke.

In one embodiment thereof, increased pulse wave velocity (PWV) is defined as an carotid-femoral aortic PWV of more than 10 m/sec, more than 10.5 m/sec, preferably more than 11 m/sec, more than 11.5 m/sec, and even more preferably of more than 12 m/sec.

In one embodiment thereof, increased pulse pressure (PP) is defined as a wide brachial pulse pressure of more than 60 mm Hg, preferably of more than 65 mm Hg, and more preferably of more than 70 mg Hg.

In another embodiment thereof, said patient also has an increased central aortic pulse pressure (CAPP or CPP) defined as a CPP of more than 50 mg Hg, preferably more than 55 mg Hg, and even more preferably of more than 60 mg Hg or more.

In another embodiment of the foregoing, said patients are aged 60 years or older, 61 years or older, 62 years or older, 63 years or older, 64 years or older, 65 years or older. Preferably the patients are aged 60 years or older.

In one embodiment, said patients have a diagnosis of essential hypertension, in particular said patients have a mean sitting systolic blood pressure (msSBP) of ≥150 and <180 mm Hg.

In another embodiment, sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

The present invention provides that the pharmaceutical composition comprising a therapeutically effective amount of sacubitril and valsartan in a 1:1 molar ratio is effective to provide reducing arterial stiffness in a patient.

The present invention also provides that the pharmaceutical composition better provides reducing arterial stiffness in a patient than the corresponding amount of an angiotensin receptor blocker, such as olmesartan, alone.

In one embodiment, the human patient also suffers from a cardiovascular disease, in particular essential hypertension.

In one aspect of the present invention which applies to all of the aforementioned treatment options, the pharmaceutical composition is administered to deliver a daily overall dose of the combination of sacubitril and valsartan in a 1:1 molar ratio from about 50 mg to about 1000 mg, in particular to about 800 mg, or to about 400 mg.

In particular, the pharmaceutical composition is administered to deliver the combination of sacubitril and valsartan in a 1:1 molar ratio once or twice daily with a dose of 50 mg, 100 mg, or 200 mg. in other words, the combination of sacubitril and valsartan in a 1:1 molar ratio is administered to the patient once or twice daily with an individual dose of 50 mg, 100 mg, or 200 mg.

In one embodiment thereof,
a) the 50 mg dose of sacubitril and valsartan in a 1:1 molar ratio corresponds to 24 mg sacubitril and 26 mg valsartan,
b) the 100 mg dose of sacubitril and valsartan in a 1:1 molar ratio corresponds to 49 mg sacubitril and 51 mg valsartan, and
c) the 200 mg dose of sacubitril and valsartan in a 1:1 molar ratio corresponds to 97 mg sacubitril and 103 mg valsartan.

In a particular embodiment of the pharmaceutical composition, the combination of sacubitril and valsartan in a 1:1 molar ratio is delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), wherein
a) the 50 mg dose of sacubitril and valsartan in a 1:1 molar ratio corresponds to around 56.6 mg LCZ696,
b) the 100 mg dose of sacubitril and valsartan in a 1:1 molar ratio corresponds to around 113.1 mg LCZ696, and
c) the 200 mg dose of sacubitril and valsartan in a 1:1 molar ratio corresponds to around 226.2 mg LCZ696.

In one embodiment of the aforementioned ones, the combination of a therapeutic agent blocking the angiotensin receptor and a therapeutic agent inhibiting the NEP enzyme is delivered in the form of pharmaceutical composition comprising in addition one or more pharmaceutically acceptable carriers.

In another embodiment, said patient is concomitantly receiving standard of care treatment for preventing or reducing risk of experiencing recurrent cardiovascular events.

In a further embodiment, said standard of care treatment comprises treatment with a stable dose of a beta-blocker, an aldosterone antagonist, and/or a diuretic.

In an alternative embodiment said standard of care treatment comprises treatment with a stable dose of a beta-blocker and optionally an aldosterone antagonist.

All the aforementioned embodiments for the methods of protection and treatment according to the present invention are equally applicable to
the use of the pharmaceutical compositions comprising a 1:1 molar ratio of sacubitril and valsartan as defined herein for the manufacture of a medicament for use according to the present invention,
the use of the pharmaceutical compositions comprising a 1:1 molar ratio of sacubitril and valsartan as defined herein according to the present invention,
the pharmaceutical compositions comprising a 1:1 molar ratio of sacubitril and valsartan as defined herein for use according to the present invention.

In particular, all the aforementioned embodiments for the methods of protection and treatment according to the present invention are equally applicable to the pharmaceutical compositions for the use in reducing arterial stiffness in a human patient according to the present invention, to the use of the pharmaceutical compositions for reducing arterial stiffness in a human patient according to the present invention and to the use of the pharmaceutical compositions for the manufacture of a medicament for reducing arterial stiffness in a human patient according to the present invention.

Some of these alternatives are depicted in the claims, which shall be considered to form part of the disclosure.

Some of these aspects are further described in more detail below, but this description should not be construed as limiting.

Compounds and Compositions for Use According to the Invention

In the context of the present invention, the term "sacubitril and valsartan in a 1:1 molar ratio" refers to a combination comprising a therapeutically effective amount of a 1:1 molar ratio of
(i) valsartan or a pharmaceutically acceptable salt thereof; and
(ii) sacubitril or a pharmaceutically acceptable salt thereof.

Sacubitril is the INN for N-(3-carboxy-1-oxopropyl)-(4S)-(p-phenylphenylmethyl)-4-amino-2R-methylbutanoic acid ethyl ester. This is a prodrug for (2R,4S)-5-biphenyl-4-yl-4-(3-carboxy-propionyl amino)-2-methyl-pentanoic acid.

Valsartan is S—N-valeryl-N-{[2'-(1H-tetrazole-5-yl)-biphenyl-4-yl]-methyl}-valine.

In one embodiment thereof, the combination comprises a
1:1 molar ratio
(i) of valsartan; and
(ii) of N-(3-carboxy-1-oxopropyl)-(4S)-(p-phenylphenyl-methyl)-4-amino-2R-methylbutanoic acid ethyl ester or a pharmaceutically acceptable salt thereof, such as sodium or calcium salt.

In another embodiment thereof, said combination is provided in the form of the compound of the formula (I)

$$[(A_1)(A_2)](Na^+)_y \cdot xH_2O \qquad (I)$$

wherein
$A_1$ is valsartan in the anionic form;
$A_2$ is sacubitril in the anionic form;
$Na^+$ is a sodium ion;
y is 1 to 3, preferably 1, 2, or 3; and
x is 0 to 3, preferably 0, 0.5, 1, 1.5, 2, 2.5, or 3.
In one embodiment, y is 3 and x is 2.5.
In particular, the compound is trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate (LCZ696).

In a preferred embodiment, the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is present in crystalline form.

In a preferred embodiment, the invention encompasses a pharmaceutical composition for use comprising a therapeutically effective amount of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate) biphenyl-4'-ylmethyl}amino)butyrate] hemipentahydrate (Compound LCZ696). Such compounds and pharmaceutical compositions have been previously disclosed in WO2007/056546 and WO 2009/061713, whose preparative teachings are incorporated herein by reference.

In a further embodiment of the invention, the pharmaceutical compositions for use according to the present invention comprise trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate (LCZ696) and deliver upon administration the NEP inhibitor pro-drug and the angiotensin receptor blocker together to the patient.

In one embodiment of the invention for all of its uses, the pharmaceutical composition comprises the the NEP inhibitor pro-drug sacubitril, namely N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof. Such combinations are for example disclosed within international patent application WO 2003/059345, which is herewith incorporated by reference.

In one embodiment, the pharmaceutical composition comprises the NEP inhibitor pro-drug sacubitril, namely N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof, in a 1:1 molar ratio.

(i) Valsartan or (S)—N-valeryl-N-{[2'-(1H-tetrazole-5-yl)-biphenyl-4-yl]-methyl}-valine) or a pharmaceutically acceptable salt thereof that can be purchased from commercial sources or can be prepared according to known methods, such as described in U.S. Pat. No. 5,399,578 and EP 0443983, whose preparative teachings are incorporated by reference herein. Valsartan may be used in certain embodiments of the invention in its free acid form, as well as in any suitable salt form. Depending upon the circumstance, esters or other derivatives of the carboxylic grouping may be employed as well as salts and derivatives of the tetrazole grouping.

(ii) sacubitril, namely N-(3-carboxy-1-oxopropyl)-(4S)-(p-phenylphenylmethyl)-4-amino-2R-methylbutanoic acid ethyl ester or (2R,4S)-5-biphenyl-4-yl-4(3-carboxy-propionyl amino)-2-methyl-pentanoic acid can be prepared by known methods such as described in U.S. Pat. No. 5,217,996 which is herein incorporated by reference.

The corresponding active ingredient or a pharmaceutically acceptable salt thereof may also be used in the form of a hydrate or include other solvents used for crystallization.

Preferably, the compounds sacubitril or a salt thereof, valsartan or a salt thereof, or LCZ696 are substantially pure or in a substantially pure form. As used herein, "substantially pure" refers to at least about 90% purity, more preferably at least about 95% and most preferably at least about 98% purity.

Also preferred is that these compounds are solid or a solid form or solid state. The solid, solid form or solid state can be crystalline, partially crystalline, amorphous or polyamorphous, preferably in the crystalline form.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carriers, especially suitable for enteral or parenteral application.

The pharmaceutical preparations of the invention contain, for example, from about 0.1% to about 100%, e.g. 80% or 90%, or from about 1% to about 60%, of the active ingredient. The term "about" or "approximately", as used herein in each instance, shall have the meaning of within 10%, more preferably within 5%, of a given value or range.

Pharmaceutical preparations according to the invention for enteral or parenteral administration are, e.g., those in unit dose forms, such as sugar-coated tablets, tablets, capsules, bars, sachets, granules, syrups, aqueous or oily suspensions or suppositories and furthermore ampoules. These are prepared in a manner known per se, e.g. by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Tablets may be formed from the active compound with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound.

Other dosage forms for oral administration include, for example, aqueous suspensions containing the active compound in an aqueous medium in the presence of a non-toxic suspending agent such as sodium carboxymethylcellulose, and oily suspensions containing the active compounds in a suitable vegetable oil, for example *arachis* oil.

The active compound may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

The dosage of the active ingredient of the composition will, of course, vary with the nature of the severity of the condition to be treated and with the particular compound in the composition and its route of administration. It will also vary according to the age, weight and response of the individual patient.

In the embodiments where the pharmaceutical composition comprises trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate (LCZ696) in the pharmaceutical compositions for use in the context of the present invention, the unit dose of the therapeutic agents sacubitril and valsartan together will be in the range from about 1 to about 1000 mg, such as 40 mg to 400 mg (e.g., 50 mg, 100 mg, 200 mg, 400 mg) per day. Alternatively lower doses may be given, for example doses of 0.5 to 100 mg; 0.5 to 50 mg; or 0.5 to 20 mg per day. As explanatory note, a unit dose of 100 mg LCZ696 delivering 100 mg of the two agents sacubitril and valsartan corresponds to 113.1 mg of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate. Correspondingly, a unit dose of 50 mg requires 56.6 mg, a unit dose of 200 mg requires 226.2 mg, and a unit dose of 400 mg requires 452.4 mg of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate, respectively.

Dosages of the sum of the individual compounds sacubitril and valsartan or their respective salts in the combination of the pharmaceutical composition will be in the range from about 1 to about 1000 mg, such as 40 mg to 400 mg and include but are not limited to 5 mg, 20 mg, 25 mg, 40 mg, 50 mg, 80 mg, 100 mg, 200 mg, 400 mg, 800 mg and 1000 mg. Such dosages for the individual compounds sacubitril and valsartan can be considered therapeutically effective amounts or dosage strengths. Ratios for the amount of each compound in the pharmaceutical composition are preferably in the about 1:1 molar ratio to achieve an optimal reduction of arterial stiffness. Ratios for the amount of each compound in the pharmaceutical composition are preferably in the about 1:1 molar ratio to achieve an therapeutic effect for the reduction of arterial stiffness. In preferred embodiments, the dosages of the individual compounds sacubitril and valsartan correspond to the same molecular amounts as in a pharmaceutical composition comprising a 50 mg, 100 mg, 200 mg or 400 mg dose of LCZ696. E.g. a 200 mg dose of LCZ696 corresponds approximately to 103 mg valsartan and 97 mg of sacubitril.

Pharmaceutical compositions as used in the current invention can be administered any number of times per day, i.e. once a day (q.d.), twice (b.i.d.), three times, four time, etc. in an immediate release formation or less frequently as an extended or sustained release formation. Preferably the pharmaceutical composition is administered twice daily (b.i.d.). Corresponding doses may be taken, for example, in the morning, at mid-day or in the evening.

EMBODIMENTS OF THE INVENTION

In particular, the present invention relates to the following embodiments:

Embodiment 1

A method of reducing arterial stiffness in a human patient showing at least one symptom selected from increased pulse wave velocity (PWV) and increased pulse pressure (PP) comprising administering to said patient a therapeutically effective amount or a prophylactically effective amount of a combination of a therapeutic agent blocking the angiotensin receptor and a therapeutic agent inhibiting the NEP enzyme.

Embodiment 2

A method according to claim 1 wherein the combination of a therapeutic agent blocking the angiotensin receptor and a therapeutic agent inhibiting the NEP enzyme comprises sacubitril and valsartan in a 1:1 molar ratio.

Embodiment 3

A method according to claim 1 or 2, wherein the method is for treating, preventing or reducing the risk of experiencing a disorder or disease selected from cognitive impairment, a cardiovascular event, a cerebrovascular event and combinations thereof.

Embodiment 4

The method according to claim 3, wherein said cognitive impairment is selected from the group consisting of mild cognitive impairment, age related cognitive function decline, and Alzheimer's disease.

Embodiment 5

The method according to claim 3, wherein said cardiovascular event is selected from the group consisting of cardiovascular death, myocardial infarction (MI), atrial fibrillation, hospitalization for unstable angina, acute coronary syndrome, other non-coronary ischemic event (transient ischemic attack or limb ischemia), any revascularization procedure (coronary and non-coronary), hospitalization or prolongation of hospitalization for heart failure, and coronary revascularization procedures.

Embodiment 6

The method according to claim 3, wherein said cerebrovascular event is stroke.

Embodiment 7

The method according to any of the preceding claims wherein increased pulse wave velocity (PWV) is defined as an carotid-femoral aortic PWV of more than 10 m/sec, preferably more than 11 m/sec, and even more preferably of more than 12 m/sec.

Embodiment 8

The method according to any of the preceding claims, wherein increased pulse pressure (PP) is defined as a wide brachial pulse pressure of more than 60 mm Hg, preferably of more than 65 mm Hg, and more preferably of more than 70 mg Hg.

Embodiment 9

The method according to any of the preceding claims, wherein said patient also has an increased central aortic pulse pressure (CPP) defined as a CPP of more than 50 mg Hg, preferably more than 55 mg Hg, and even more preferably of more than 60 mg Hg.

Embodiment 10

The method according to any of the preceding claims, wherein said patients are aged 60 years or older.

Embodiment 11

The method according to any of the preceding claims, wherein said patients have a diagnosis of essential hypertension, in particular said patients have a mean sitting systolic blood pressure (msSBP) of ≥150 and <180 mm Hg.

Embodiment 12

The method according to any one of the preceding claims 2 to 11, wherein the combination of sacubitril and valsartan in a 1:1 molar ratio is delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

Embodiment 13

The method according to any one of the preceding claims 2 to 12, wherein the therapeutically effective amount or the prophylactically effective amount of a combination of sacubitril and valsartan in a 1:1 molar ratio comprises a daily overall dose of the combination of sacubitril and valsartan in a 1:1 molar ratio from about 50 mg to about 1000 mg.

Embodiment 14

The method according to claim 13, wherein the combination of sacubitril and valsartan in a 1:1 molar ratio is administered to the patient once or twice daily with an individual dose of 50 mg, 100 mg, or 200 mg.

Embodiment 15

The method according to claim 14, wherein
a) the 50 mg dose of sacubitril and valsartan in a 1:1 molar ratio corresponds to 24 mg sacubitril and 26 mg valsartan,
b) the 100 mg dose of sacubitril and valsartan in a 1:1 molar ratio corresponds to 49 mg sacubitril and 51 mg valsartan, and
c) the 200 mg dose of sacubitril and valsartan in a 1:1 molar ratio corresponds to 97 mg sacubitril and 103 mg valsartan.

Embodiment 16

The method according to claim 15, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), and wherein
a) the 50 mg dose of sacubitril and valsartan in a 1:1 molar ratio corresponds to around 56.6 mg LCZ696,
b) the 100 mg dose of sacubitril and valsartan in a 1:1 molar ratio corresponds to around 113.1 mg LCZ696, and
c) the 200 mg dose of sacubitril and valsartan in a 1:1 molar ratio corresponds to around 226.2 mg LCZ696.

Embodiment 17

The method according to any one of the preceding claims, wherein the combination of a therapeutic agent blocking the angiotensin receptor and a therapeutic agent inhibiting the NEP enzyme is delivered in the form of pharmaceutical composition comprising in addition one or more pharmaceutically acceptable carriers.

Embodiment 18

The method according to any one of the preceding claims, wherein said patient is concomitantly receiving standard of care treatment for preventing or reducing risk of experiencing recurrent cardiovascular events.

Embodiment 19

The method according to claim 18, wherein said standard of care treatment comprises treatment with a stable dose of a beta-blocker, an aldosterone antagonist, and/or a diuretic.

Embodiment 20

The method according to claim 18, wherein said standard of care treatment comprises treatment with a stable dose of a beta-blocker and optionally an aldosterone antagonist.

Embodiment 21

A pharmaceutical composition comprising a therapeutically effective amount or a prophylactically effective amount of a combination of a therapeutic agent blocking the angiotensin receptor and a therapeutic agent inhibiting the NEP enzyme for use in reducing arterial stiffness in a human patient showing at least one symptom selected from increased pulse wave velocity (PWV) and increased pulse pressure (PP).

Embodiment 22

The pharmaceutical composition for use according to claim 21, wherein the combination of a therapeutic agent blocking the angiotensin receptor and a therapeutic agent inhibiting the NEP enzyme comprises sacubitril and valsartan in a 1:1 molar ratio Embodiment 23

The pharmaceutical composition for use according to claim 21 or 22, wherein the use is for treating, preventing or reducing the risk of experiencing a disorder or disease selected from cognitive impairment, a cardiovascular event, a cerebrovascular event and combinations thereof.

Embodiment 24

The pharmaceutical composition for use according to claim 23, wherein said cognitive impairment is selected from the group consisting of mild cognitive impairment, age related cognitive function decline, and Alzheimer's disease.

Embodiment 25

The pharmaceutical composition for use according to claim 23, wherein said cardiovascular event is selected from the group consisting of cardiovascular death, myocardial infarction (MI), atrial fibrillation, hospitalization for unstable angina, acute coronary syndrome, other non-coronary ischemic event (transient ischemic attack or limb ischemia), any revascularization procedure (coronary and non-coronary), hospitalization or prolongation of hospitalization for heart failure, and coronary revascularization procedures.

Embodiment 26

The pharmaceutical composition for use according to claim 23, wherein said cerebrovascular event is stroke.

Embodiment 27

The pharmaceutical composition for use according to any of the preceding claims 21 to 26, wherein increased pulse wave velocity (PWV) is defined as an carotid-femoral aortic PWV of more than 10 m/sec, preferably more than 11 m/sec, and even more preferably of more than 12 m/sec.

Embodiment 28

The pharmaceutical composition for use according to any of the preceding claims 21 to 27, wherein increased pulse pressure (PP) is defined as a wide brachial pulse pressure of more than 60 mm Hg, preferably of more than 65 mm Hg, and more preferably of more than 70 mg Hg.

Embodiment 29

The pharmaceutical composition for use according to any of the preceding claims 21 to 28, wherein said patient also has an increased central aortic pulse pressure (CPP) defined as a CPP of more than 50 mg Hg, preferably more than 55 mg Hg, and even more preferably of more than 60 mg Hg.

Embodiment 30

The pharmaceutical composition for use according to any of the preceding claims 21 to 29, wherein said patients are aged 60 years or older.

Embodiment 31

The pharmaceutical composition for use according to any of the preceding claims 21 to 30, wherein said patients have a diagnosis of essential hypertension, in particular said patients have a mean sitting systolic blood pressure (msSBP) of ≥50 and <180 mm Hg.

Embodiment 32

The pharmaceutical composition for use according to any one of the preceding claims 22 to 31, wherein the combination of sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

Embodiment 33

The pharmaceutical composition for use according to any one of the preceding claims 22 to 32, wherein the therapeutically effective amount or the prophylactically effective amount of a combination of sacubitril and valsartan in a 1:1 molar ratio comprises a daily overall dose of the combination of sacubitril and valsartan in a 1:1 molar ratio from about 50 mg to about 1000 mg.

Embodiment 34

The pharmaceutical composition for use according to claim 33, wherein the combination of sacubitril and valsartan in a 1:1 molar ratio is administered to the patient once or twice daily with an individual dose of 50 mg, 100 mg, or 200 mg.

Embodiment 35

The pharmaceutical composition for use according to claim 34, wherein
  a) the 50 mg dose of sacubitril and valsartan in a 1:1 molar ratio corresponds to 24 mg sacubitril and 26 mg valsartan,
  b) the 100 mg dose of sacubitril and valsartan in a 1:1 molar ratio corresponds to 49 mg sacubitril and 51 mg valsartan, and
  c) the 200 mg dose of sacubitril and valsartan in a 1:1 molar ratio corresponds to 97 mg sacubitril and 103 mg valsartan.

Embodiment 36

The pharmaceutical composition for use according to claim 35, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), and wherein
  a) the 50 mg dose of sacubitril and valsartan in a 1:1 molar ratio corresponds to around 56.6 mg LCZ696,
  b) the 100 mg dose of sacubitril and valsartan in a 1:1 molar ratio corresponds to around 113.1 mg LCZ696, and
  c) the 200 mg dose of sacubitril and valsartan in a 1:1 molar ratio corresponds to around 226.2 mg LCZ696.

Embodiment 37

The pharmaceutical composition for use according to any one of the preceding claims 21 to 36, wherein the pharmaceutical composition comprises in addition one or more pharmaceutically acceptable carriers.

Embodiment 38

The pharmaceutical composition for use according to any one of the preceding claims 21 to 37, wherein said patient is concomitantly receiving standard of care treatment for preventing or reducing risk of experiencing recurrent cardiovascular events.

Embodiment 39

The pharmaceutical composition for use according to claim 38, wherein said standard of care treatment comprises treatment with a stable dose of a beta-blocker, an aldosterone antagonist, and/or a diuretic.

Embodiment 40

The pharmaceutical composition for use according to claim 38, wherein said standard of care treatment comprises treatment with a stable dose of a beta-blocker and optionally an aldosterone antagonist.

Embodiment 41

Use of a pharmaceutical composition comprising a therapeutically effective amount or a prophylactically effective amount of a combination of a therapeutic agent blocking the angiotensin receptor and a therapeutic agent inhibiting the NEP enzyme for the manufacture of a medicament for reducing arterial stiffness in a human patient showing at least one symptom selected from increased pulse wave velocity (PWV) and increased pulse pressure (PP).

Embodiment 42

Use of a pharmaceutical composition according to claim 41, wherein the combination of a therapeutic agent blocking the angiotensin receptor and a therapeutic agent inhibiting the NEP enzyme comprises sacubitril and valsartan in a 1:1 molar ratio

Embodiment 43

Use of a pharmaceutical composition according to claim 41 or 42, wherein the medicament is for treating, preventing or reducing the risk of experiencing a disorder or disease selected from cognitive impairment, a cardiovascular event, a cerebrovascular event and combinations thereof.

Embodiment 44

Use of a pharmaceutical composition according to claim 43, wherein said cognitive impairment is selected from the group consisting of mild cognitive impairment, age related cognitive function decline, and Alzheimer's disease.

Embodiment 45

Use of a pharmaceutical composition according to claim 43, wherein said cardiovascular event is selected from the group consisting of cardiovascular death, myocardial infarction (MI), atrial fibrillation, hospitalization for unstable angina, acute coronary syndrome, other non-coronary ischemic event (transient ischemic attack or limb ischemia), any revascularization procedure (coronary and non-coronary), hospitalization or prolongation of hospitalization for heart failure, and coronary revascularization procedures.

Embodiment 46

Use of a pharmaceutical composition according to claim 43, wherein said cerebrovascular event is stroke.

Embodiment 47

Use of a pharmaceutical composition according to any of the preceding claims 41 to 46, wherein increased pulse wave velocity (PWV) is defined as an carotid-femoral aortic PWV of more than 10 m/sec, preferably more than 11 m/sec, and even more preferably of more than 12 m/sec.

Embodiment 48

Use of a pharmaceutical composition according to any of the preceding claims 41 to 47, wherein increased pulse pressure (PP) is defined as a wide brachial pulse pressure of more than 60 mm Hg, preferably of more than 65 mm Hg, and more preferably of more than 70 mg Hg.

Embodiment 49

Use of a pharmaceutical composition according to any of the preceding claims 41 to 48, wherein said patient also has an increased central aortic pulse pressure (CPP) defined as a CPP of more than 50 mg Hg, preferably more than 55 mg Hg, and even more preferably of more than 60 mg Hg.

Embodiment 50

Use of a pharmaceutical composition according to any of the preceding claims 41 to 49, wherein said patients are aged 60 years or older.

Embodiment 51

Use of a pharmaceutical composition according to any of the preceding claims 41 to 50, wherein said patients have a diagnosis of essential hypertension, in particular said patients have a mean sitting systolic blood pressure (msSBP) of ≥150 and <180 mm Hg.

Embodiment 52

Use of a pharmaceutical composition according to any one of the preceding claims 42 to 51, wherein the combination of sacubitril and valsartan in a 1:1 molar ratio is delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

Embodiment 53

Use of a pharmaceutical composition according to any one of the preceding claims 42 to 52, wherein the therapeutically effective amount or the prophylactically effective amount of a combination of sacubitril and valsartan in a 1:1 molar ratio comprises a daily overall dose of the combination of sacubitril and valsartan in a 1:1 molar ratio from about 50 mg to about 1000 mg.

Embodiment 54

Use of a pharmaceutical composition according to claim 53, wherein the combination of sacubitril and valsartan in a 1:1 molar ratio is administered to the patient once or twice daily with an individual dose of 50 mg, 100 mg, or 200 mg.

Embodiment 55

Use of a pharmaceutical composition according to claim 54, wherein
 a) the 50 mg dose of sacubitril and valsartan in a 1:1 molar ratio corresponds to 24 mg sacubitril and 26 mg valsartan,
 b) the 100 mg dose of sacubitril and valsartan in a 1:1 molar ratio corresponds to 49 mg sacubitril and 51 mg valsartan, and
 c) the 200 mg dose of sacubitril and valsartan in a 1:1 molar ratio corresponds to 97 mg sacubitril and 103 mg valsartan.

Embodiment 56

Use of a pharmaceutical composition according to claim 55, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), and wherein
  a) the 50 mg dose of sacubitril and valsartan in a 1:1 molar ratio corresponds to around 56.6 mg LCZ696,
  b) the 100 mg dose of sacubitril and valsartan in a 1:1 molar ratio corresponds to around 113.1 mg LCZ696, and
  c) the 200 mg dose of sacubitril and valsartan in a 1:1 molar ratio corresponds to around 226.2 mg LCZ696.

Embodiment 57

Use of a pharmaceutical composition according to any one of the preceding claims 41 to 56, wherein the pharmaceutical composition comprises in addition one or more pharmaceutically acceptable carriers.

Embodiment 58

Use of a pharmaceutical composition according to any one of the preceding claims 41 to 57, wherein said patient is concomitantly receiving standard of care treatment for preventing or reducing risk of experiencing recurrent cardiovascular events.

Embodiment 59

Use of a pharmaceutical composition according to claim 58, wherein said standard of care treatment comprises treatment with a stable dose of a beta-blocker, an aldosterone antagonist, and/or a diuretic.

Embodiment 60

Use of a pharmaceutical composition according to claim 58, wherein said standard of care treatment comprises treatment with a stable dose of a beta-blocker and optionally an aldosterone antagonist.

The following example is illustrative, but does not serve to limit the scope of the invention described herein.

Example 1

A Phase 2, multi-center, randomized, double-blind, active-controlled, parallel-group, study to evaluate the efficacy and safety of LCZ696 compared to olmesartan in elderly patients (≥60 years) with essential hypertension (mean sitting systolic blood pressure [msSBP] ≥150 mmHg and <180 mmHg and pulse pressure [PP]>60 mmHg). The inclusion criteria in the study was designed to enroll patients which met the profile of elderly patients with systolic hypertension and a wide pulse pressure, a characteristic reflective of large artery (aortic) stiffness. The study consisted of 2 measurement time points: 12 weeks and 52 weeks, in order to assess the short and long-term influence of LCZ696 on measures of central blood pressure (BP) and arterial stiffness beyond its effect to lower peripheral BP in elderly hypertensive patients. The study enrolled patient from 5 Dec. 2012 to 8 Apr. 2015. These first interpretable results (FIR) describe the baseline demographics, primary and key secondary endpoints, as well as safety endpoints (ClinicalTrials.gov Identifier: NCT01692301).

Study Drug LCZ696:

LCZ696 refers to the supramolecular complex trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate. This compound and pharmaceutical compositions thereof have been previously disclosed in WO2007/056546 and WO 2009/061713, whose preparative teachings are incorporated herein by reference.

LCZ696 is a first-in-class angiotensin receptor neprilysin inhibitor that comprises the molecular moieties of the NEP (neutral endopeptidase EC 3.4.24.11) inhibitor pro-drug AHU377 (N-(3-carboxy-1-oxopropyl)-(4S)-p-phenylphenylmethyl)-4-amino-(2R)-methylbutanoic acid ethyl ester) and the angiotensin receptor blocker valsartan as a single compound. AHU377 is metabolized by enzymatic cleavage to LBQ657 (N-(3-carboxy-1-oxopropyl)-(4S)-p-phenylphenylmethyl)-4-amino-(2R)-methylbutanoic acid), the active inhibitor of neutral endopeptidase, which is the major enzyme responsible for the breakdown of atrial natriuretic peptides.

Comparator Drug Olmesartan:

Olmesartan can be purchased from commercial sources. Olmesartan is approved for the treatment of hypertension.

Overall Study Design:

This was a 52-week study, involving 50 centers from 12 countries (across Europe, South America, Asia and the United States). The study included a screening epoch, a placebo run-in epoch, and an initial double-blind treatment epoch of 12 weeks with LCZ696 monotherapy, followed by a double-blind extension epoch of 40 weeks. Patients were randomized to receive either once daily LCZ696 200 mg or olmesartan 20 mg for 4 weeks, followed by a forced titration to double the initial doses for the next 8 weeks. After 12 weeks, patients with uncontrolled BP (msSBP>140 mmHg and/or mean sitting diastolic blood pressure [msDBP]>90 mmHg) were allowed the use of add-on antihypertensives (amlodipine [2.5-5.0 mg] and then hydrochlorothiazide [6.25-25.0 mg]) as needed, at an interval of 4 weeks up to Week 24.

The primary and secondary endpoints are changes from baseline in central aortic systolic pressure (CASP) and central aortic PP (CAPP) at week 12, respectively. Other secondary endpoints are the changes in CASP and CAPP at week 52. A sample size of 432 randomised patients is estimated to ensure a power of 90% to assess the superiority of LCZ696 over olmesartan at week 12 in the change from baseline of mean CASP, assuming an SD of 19 mm Hg, the difference of 6.5 mm Hg and a 15% dropout rate. The primary variable will be analysed using a two-way analysis of covariance.

Study Patients

Elderly patients (aged 60 years) with essential hypertension (either untreated or treated with antihypertensive agents) and patients who have msSBP≥150 mm Hg and <180 mm Hg at randomisation are eligible for inclusion in the study. Untreated patients (if they are newly diagnosed or have not been treated with antihypertensive drugs for the 4 weeks prior to screening) must have msSBP≥50 mm Hg and <180 mm Hg at screening and randomisation, whereas patients who have been treated with antihypertensive agents 4 weeks prior to screening must have msSBP≥140 mm Hg and <180 mm Hg after 1 or 2 weeks of washout/placebo run-in and ≥150 mm Hg and <180 mm Hg at randomisation. All patients must have a PP>60 mm Hg at randomisation.

Patients with malignant or severe hypertension, secondary causes of hypertension, history of atrial fibrillation or atrial flutter during the 3 months prior to screening, or active atrial fibrillation or atrial flutter on electrocardiogram, history of CV disease (e.g., myocardial infarction) during 12 months prior to screening, and evidence of severe renal impairment (e.g., estimated glomerular filtration rate [eGFR]<30 ml/min/1.73 m2) are excluded—boxes 1 and 2 summarise the inclusion and exclusion criteria, respectively. Patients have to provide a written informed consent before starting any study-related procedures.

Study Procedures:

The details of the study design were published in Williams B, Cockcroft J R, Kario K, Zappe D H, et al. BMJ Open. 2014 Feb. 4; 4(2), which is hereby incorporated by reference in its entirety.

The Study Objectives and Endpoints

The primary objective of the study was to demonstrate the superiority of a LCZ696-based treatment regimen over an olmesartan-based treatment regimen in reducing mean CASP after 12 weeks of treatment. Superiority testing is also planned for the key secondary efficacy assessment, i.e. the reduction in mean central aortic PP (CAPP) after 12 weeks of treatment, and other secondary efficacy assessments such as mean CASP and CAPP after 52 weeks of treatment. Mean aPWV, msSBP, msDBP, msPP, mean ambulatory (ma) BP, maPP, and MAP will also be measured after 12 and 52 weeks of treatment.

Exploratory assessments comparing the two treatments after 12 and 52 weeks of treatment include pulse wave analysis (PWA) variables such as augmentation index (AIx), augmentation pressure, PP amplification ratio, duration of left ventricle (LV) ejection, and time to wave reflection; reduction in ma central (mac) BP, macMAP, and macPP; plasma biomarkers including NT-proBNP and urinary cyclic guanosine monophosphate (cGMP)/creatinine ratio and other biomarkers related to hypertension.

Haemodynamic Measurements

The SphygmoCor X-CEL System (AtCor Medical, Sydney, Australia) is being used to non-invasively derive the ascending aortic pressure waveform from the brachial waveform using a validated generalised transfer function (GTF).22 A properly sized BP cuff is linked to a computer and software and the CASP, CAPP, augmentation pressure, and AIx are determined from the analysis of waveform by the system software.

The SphygmoCor X-CEL system also measures the carotid-femoral aPWV, as the speed of the arterial pressure waveform as it travels through the descending aorta to the femoral artery, which is detected from simultaneously measured carotid and femoral arterial pulses. The carotid pulse is detected by applanation tonometry using a high-fidelity pressure transducer (Millar Instruments, Houston, Tex.), while the femoral pulse is detected using a partially inflated blood pressure cuff wrapped around the upper thigh. The distance traveled by the pulse wave is captured by making physical measurements on the body surface according to the manufacturer's recommendations. This new brachial cuff-based device with an individualised sub-diastolic cuff pressure has recently been validated against the SphygmoCor device (AtCor Medical) using the classical radial tonometry-based methodology, and provides an operator-independent method to assess systolic pressure and aortic waveform comparable with the existing validated tonometric-based methods.23 Measurements using SphygmoCor X-CEL system will be performed at baseline, randomisation, Week 12 or at the time of early discontinuation prior to Week 12, Week 52, or at the time of early discontinuation between Week 12 and Week 52.

The 24-hour maCAP and maPWA will be monitored using the oscillometric device, Mobil-0-Graph (IEM, Stolberg, Germany) with integrated ARC solver algorithms (Austrian Institute of Technology, Vienna, Austria). The traditional Mobil-O-Graph ambulatory blood pressure monitoring (ABPM) device has been available for more than a decade and through several product generations.24-27 The actual blood pressure measuring unit was validated according to the British Hypertension Society (BHS) and the European Society of Hypertension (ESH) recommendations.24,26 The method equipped with a GTF to derive aortic pressure waveforms28 is based on brachial readings acquired in the course of the conventional pressure measurement at diastolic level.

During the signal acquisition procedure, the received raw signals are separated into single waves and checked for their plausibility by means of extreme values and corresponding wavelengths using a cross-correlation approach. Poor waveforms are removed from further processing. After applying the GTF to each single waveform, the procedure is repeated. After final coherence verification, the quality judgment of grade '1' states that at least 80% of the waveforms were found to be eligible for further processing, while grades '2' and '3' represent a $\geq 50\%$, and $<50\%$ valid waveforms, respectively.29

Surrogates derived by this technique have been validated against solid-state catheter measurements and/or compared with non-invasive readings (e.g., tonometry, echocardiography) for aortic pressures,29-32 wave reflections,33 or aPWV.34,35 However, potential clinical usefulness has been demonstrated recently.36-38 Furthermore, feasibility35 and reproducibility39 of cuff-based maPWA measurements have been reported. With respect to legal issues, the Mobil-O-Graph maPWA monitor with integrated ARC solver algorithms holds approvals from CE, FDA, and JPAL (amongst others).

Safety Assessments

Safety and tolerability assessments include regular monitoring and recording of all adverse events (AEs) and concomitant medications or significant non-drug therapies. Evaluations of routine blood chemistries, blood counts with white cell differential and urine analyses, physical examinations, electrocardiograms (ECGs), and monitoring of vital signs will be performed at regular intervals.

Statistical Analysis Plan

A sample size of 183 completers per group is targeted, which is calculated based on the primary efficacy variable, change from baseline in mean CASP at 12 weeks, assuming a standard deviation of 19 mm Hg. The sample size is calculated to ensure a power of 90% to detect statistical significance for the comparison of LCZ696-based treatment regimen with the olmesartan-based treatment regimen in assessing the superiority at the Week 12 endpoint. Assuming a 15% dropout rate, the total targeted sample size to be randomised is 432 patients (216 per group). The primary variable at the Week 12 endpoint will be analysed using a two-way analysis of covariance (ANCOVA), with treatment and region as factors and the baseline as a covariate. Mean CAPP at the Week 12 endpoint will be analysed using the same type of ANCOVA model used for the primary efficacy analysis. A two-sided significance at 0.05 level will be used for this analysis and a 95% confidence interval for the treatment difference will be provided.

Results:

Subjects

A total of 454 patients were randomized into the study, of which 367 (80.8%) completed the initial and extended double-blind treatment epoch (52 weeks). The percentages of patients who discontinued during the 52-week study duration were similar between the treatment groups. Overall, the main reasons for discontinuation were due to patient's or guardian's decision to withdraw from the study (6.8%) and due to any adverse events (AE, 5.9%).

Randomized set (RAN) was defined as those patients who received a randomization number regardless of receiving double-blind study medication. All randomized patients were included in the Safety Set (SAF) and Full Analysis Set (FAS). Patients without any major PDs impacting the Week 12 analysis were defined and used as the Per Protocol Set (PPS). This supplemental efficacy population was used to assess the robustness of the primary analysis results. A total of 83% patients (LCZ696: 82.5%; olmesartan: 83.6%) had no major PDs at Week 12 and were included in the 12-week PPS (Table 1).

TABLE 1

Analysis populations (Randomized set)

| Analysis Population | LCZ696<br>N = 229<br>n (%) | Olmesartan<br>N = 225<br>n (%) | Total<br>N = 454<br>n (%) |
|---|---|---|---|
| Randomized set (RAN) | 229 (100) | 225 (100) | 454 (100) |
| Full analysis set (FAS) | 229 (100) | 225 (100) | 454 (100) |
| Safety set (SAF) | 229 (100) | 225 (100) | 454 (100) |
| 12-week per-protocol set (PPS) | 189 (82.5) | 188 (83.6) | 377 (83.0) |

Percentages are computed using the number of randomized subjects in each treatment group as the denominator.

Baseline demographics and background characteristics: The 2 treatment groups were similar with respect to the baseline demographic and background characteristics. The majority of the patients were Caucasian (64.3%). A total of 65% of the patients were over the age of 65 years with 13.0% over the age of 75 years. Patients were equally distributed by the genders. Excluding patients without hypertension history, the mean duration of hypertension was 11.9 years. Overall, 13.7% of the patients had baseline eGFR<60 ml/min/1.73 m2 and 28.6% had a history of diabetes.

Baseline office, 24-hour ambulatory (ABPM) and central blood pressure variables are presented in Table 2. The two treatment groups were similar with respect to the baseline blood pressure variables.

TABLE 2

Baseline characteristics of central and peripheral blood pressures and aortic stiffness (FAS)

| Parameter Statistic | LCZ696<br>N = 229 | Olmesartan<br>N = 225 | Total<br>N = 454 |
|---|---|---|---|
| Mean central aortic systolic blood pressure (CASP) (mmHg) | | | |
| n | 226 | 220 | 446 |
| Mean | 144.0 | 144.9 | 144.45 |
| SD | 12.65 | 12.63 | 12.64 |
| Mean central aortic diastolic blood pressure (CADP) (mmHg) | | | |
| n | 226 | 220 | 446 |
| Mean | 89.0 | 91.1 | 90.1 |
| SD | 9.58 | 10.24 | 9.95 |
| Mean central pulse pressure (CPP) (mmHg) | | | |
| n | 226 | 220 | 446 |
| Mean | 54.97 | 53.78 | 54.38 |
| SD | 11.86 | 12.95 | 12.41 |
| Mean pulse wave velocity (PWV) (m/sec) | | | |
| n | 214 | 214 | 428 |
| Mean | 10.30 | 10.17 | 10.24 |
| SD | 2.11 | 1.91 | 2.01 |
| Mean sitting systolic blood pressure (msSBP) (mmHg) | | | |
| n | 229 | 225 | 454 |
| Mean | 161.1 | 161.8 | 161.45 |
| SD | 7.10 | 7.08 | 7.09 |
| Mean sitting diastolic blood pressure (msDBP) (mmHg) | | | |
| n | 229 | 225 | 454 |
| Mean | 86.7 | 87.7 | 87.2 |
| SD | 9.0 | 9.03 | 9.01 |
| Mean sitting pulse pressure (msPP) (mmHg) | | | |
| n | 229 | 225 | 454 |
| Mean | 74.35 | 74.14 | 74.25 |
| SD | 9.89 | 10.33 | 10.10 |
| Mean sitting arterial pressure (MAP) (mmHg) | | | |
| n | 229 | 225 | 454 |
| Mean | 111.53 | 112.38 | 111.95 |
| SD | 7.00 | 6.88 | 6.95 |
| 24-hour maSBP (mmHg) | | | |
| n | 164 | 162 | 326 |
| Mean | 145.3 | 144.6 | 145.0 |
| SD | 14.01 | 12.83 | 13.42 |
| 24-hour maDBP (mmHg) | | | |
| n | 164 | 162 | 326 |
| Mean | 85.7 | 86.6 | 86.2 |
| SD | 10.11 | 9.42 | 9.8 |
| 24-hour maPP (mmHg) | | | |
| n | 164 | 162 | 326 |
| Mean | 59.6 | 58.0 | 58.8 |
| SD | 11.19 | 11.29 | 11.25 |

SD = standard deviation.
Baseline values for 24-hour ABPM were patients who also had a successful Week 12 ABPM measure.

Primary Objective: Central Aortic Systolic Pressure (CASP) at Week 12

The primary objective was to evaluate the efficacy of the LCZ696 regimen in elderly patients with essential hypertension by testing the hypothesis that the reduction in mean CASP was superior to that for the corresponding olmesartan regimen after 12 weeks of treatment.

The primary variable at Week 12 endpoint was analyzed using a 2-way analysis of covariance (ANCOVA) model with treatment and region as 2 factors, and the baseline as a covariate. To assess whether LCZ696 was superior to olmesartan, the pair-wise treatment comparison was made based on this model. The null hypothesis tested was that the mean reduction for the LCZ696 regimen was equal to the mean reduction for the olmesartan regimen versus the alternative hypothesis that they were not equal.

The superiority of LCZ696 to olmesartan regimen was achieved since the change from baseline in mean CASP at Week 12 endpoint was −12.57 mmHg in the LCZ696 group compared to −8.90 mmHg in the olmesartan group (Table 3 and FIG. 1, left side). The difference between the treatment groups was statistically significant in favor of LCZ696 (LSM difference:—3.66 mmHg; p=0.010).

TABLE 3

Change from baseline in mean CASP at Week 12 endpoint (FAS)

| Treatment Group | n | LSM change from baseline (SE) |
|---|---|---|
| LCZ696 | 207 | −12.57 (1.01) |
| Olmesartan | 206 | −8.90 (1.01) |

| Treatment Comparison | LSM difference in change from baseline (SE) | 95% CI for LSM difference |
|---|---|---|
| LCZ696 vs Olmesartan | −3.66 (1.42) | (−6.45, −0.87) p-value: 0.010* |

Least squares means (LSM), standard error (SE), confidence intervals (CI), and p-values were from an ANCOVA model with treatment and region as factors, and the baseline as a covariate.
*indicates statistical significance at 0.05 level.

Secondary Objectives: Central Pulse Pressure (CPP) at Week 12

The superiority of LCZ696 to olmesartan regimen was achieved since the change from baseline in mean CPP at Week 12 endpoint was −6.41 mmHg in the LCZ696 group compared to −3.96 mmHg in the olmesartan group (Table 4 and FIG. 1, right side). The difference between the treatment groups was statistically significant in favor of LCZ696 (LSM difference: −2.45 mmHg; p=0.012).

TABLE 4

Change from baseline in mean CPP at Week 12 endpoint (FAS)

| Treatment Group | n | LSM change from baseline (SE) |
|---|---|---|
| LCZ696 | 207 | −6.41 (0.69) |
| Olmesartan | 206 | −3.96 (0.69) |

| Treatment Comparison | LSM difference in change from baseline (SE) | 95% CI for LSM difference |
|---|---|---|
| LCZ696 vs Olmesartan | −2.45 (0.96) | (−4.34, −0.55) p-value: 0.012* |

Least squares means (LSM), standard error (SE), confidence intervals (CI), and p-values were from an ANCOVA model with treatment and region as factors, and the baseline as a covariate.
*indicates statistical significance at 0.05 level.

Secondary Objectives: Central Aortic Systolic Pressure (CASP) at Week 52

The change from baseline in mean CASP at Week 52 endpoint was numerically higher in the LCZ696 group (−16.18 mmHg) compared to the olmesartan group (−14.70 mmHg) (Table 5). However, the difference between the treatment groups was not statistically significant for LCZ696.

TABLE 5

Change from baseline in mean CASP at Week 52 endpoint (FAS)

| Treatment Group | n⁺ | LSM change from baseline (SE) |
|---|---|---|
| LCZ696 | 209 | −16.18 (0.96) |
| Olmesartan | 208 | −14.70 (0.96) |

| Treatment Comparison | LSM difference in change from baseline (SE) | 95% CI for LSM difference |
|---|---|---|
| LCZ696 vs Olmesartan | −1.49 (1.35) | (−4.14, 1.16) p-value: 0.271 |

Least squares means (LSM), standard error (SE), confidence intervals (CI), and p-values were from an ANCOVA model with treatment and region as factors, and the baseline as a covariate. For the measurement at Week 52 endpoint, the last observation carried forward (LOCF) method was used to include all patients who had at least one post baseline efficacy assessment.
⁺Four patients did not have a successful SphygmoCor (CASP) assessment at Week 12 but passed QC at Week 52, thus 4 more patients were included in the Week 52 Endpoint analysis.
*indicates statistical significance at 0.05 level.

Secondary Objectives: Central Pulse Pressure (CPP) at Week 52

The change from baseline in mean CPP at Week 52 endpoint was numerically higher in the LCZ696 group (−7.16 mmHg) compared to the olmesartan group (−6.65 mmHg) (Table 6). However, the difference between the treatment groups was not statistically significant for LCZ696.

TABLE 6

Change from baseline in mean CPP at Week 52 endpoint (FAS)

| Treatment Group | n⁺ | LSM change from baseline (SE) |
|---|---|---|
| LCZ696 | 209 | −7.16 (0.69) |
| Olmesartan | 208 | −6.65 (0.69) |

| Treatment Comparison | LSM difference in change from baseline (SE) | 95% CI for LSM difference |
|---|---|---|
| LCZ696 vs Olmesartan | −0.51 (0.97) | (−2.42, 1.40) p-value: 0.598 |

Least squares means (LSM), standard error (SE), confidence intervals (CI), and p-values were from an ANCOVA model with treatment and region as factors, and the baseline as a covariate. For the measurement at Week 52 endpoint, the last observation carried forward (LOCF) method was employed to include all patients who had at least one post baseline efficacy assessment.
⁺Four patients did not have a successful SphygmoCor (CASP) assessment at Week 12 but passed QC at Week 52, thus 4 more patients were included in the Week 52 Endpoint analysis.
*indicates statistical significance at 0.05 level.

Further Outcome Measures—Hemodynamic Changes

Figure 2:
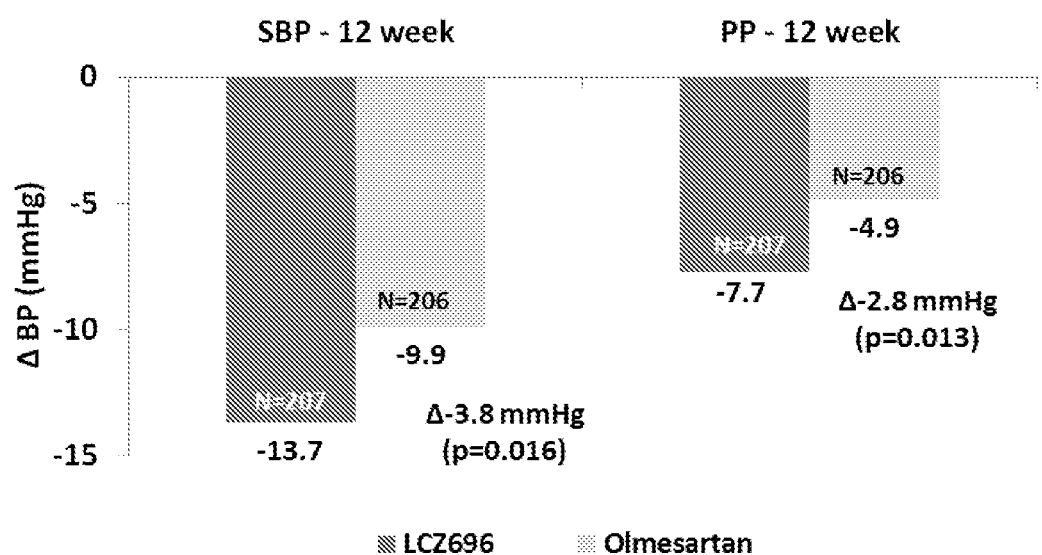
FIG. 2: Change in brachial SBP and PP at Week 12. Abbreviations: BP, blood pressure; PP, pulse pressure; SBP, systolic blood pressure
Figure 3:
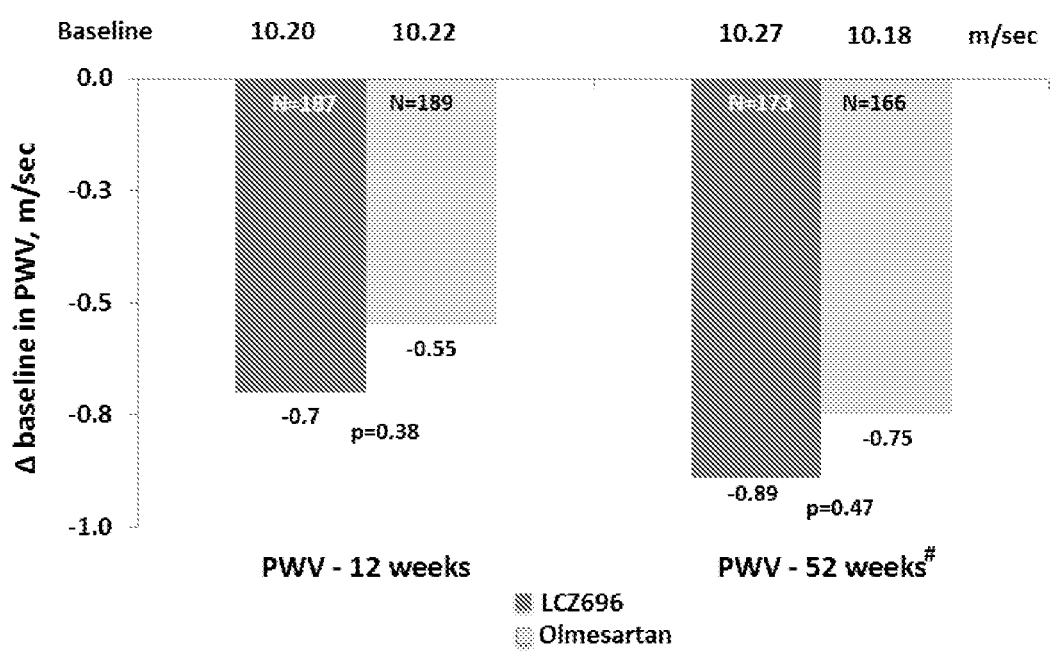
FIG. 3: Change from baseline in PWV at Week 12 and 52. Abbreviations: #regimen allowed add-on amlodipine/HCTZ for added BP control; ANCOVA model included treatment, region, and baseline PWV as covariates; at each time point, only subjects with a value at both baseline and this time point are included; PWV, pulse wave velocity.

All Hemodynamic changes from baseline at Weeks 12 and 52 are summarized in Table 7. FIG. 2 shows changes in brachial SBP and PP at Week 12. And FIG. 3 shows changes from baseline in PWV at Week 12 and 52.

Detailed Analysis: For PWV and SBP, a Quartile Analysis was Performed.

Figure 4:
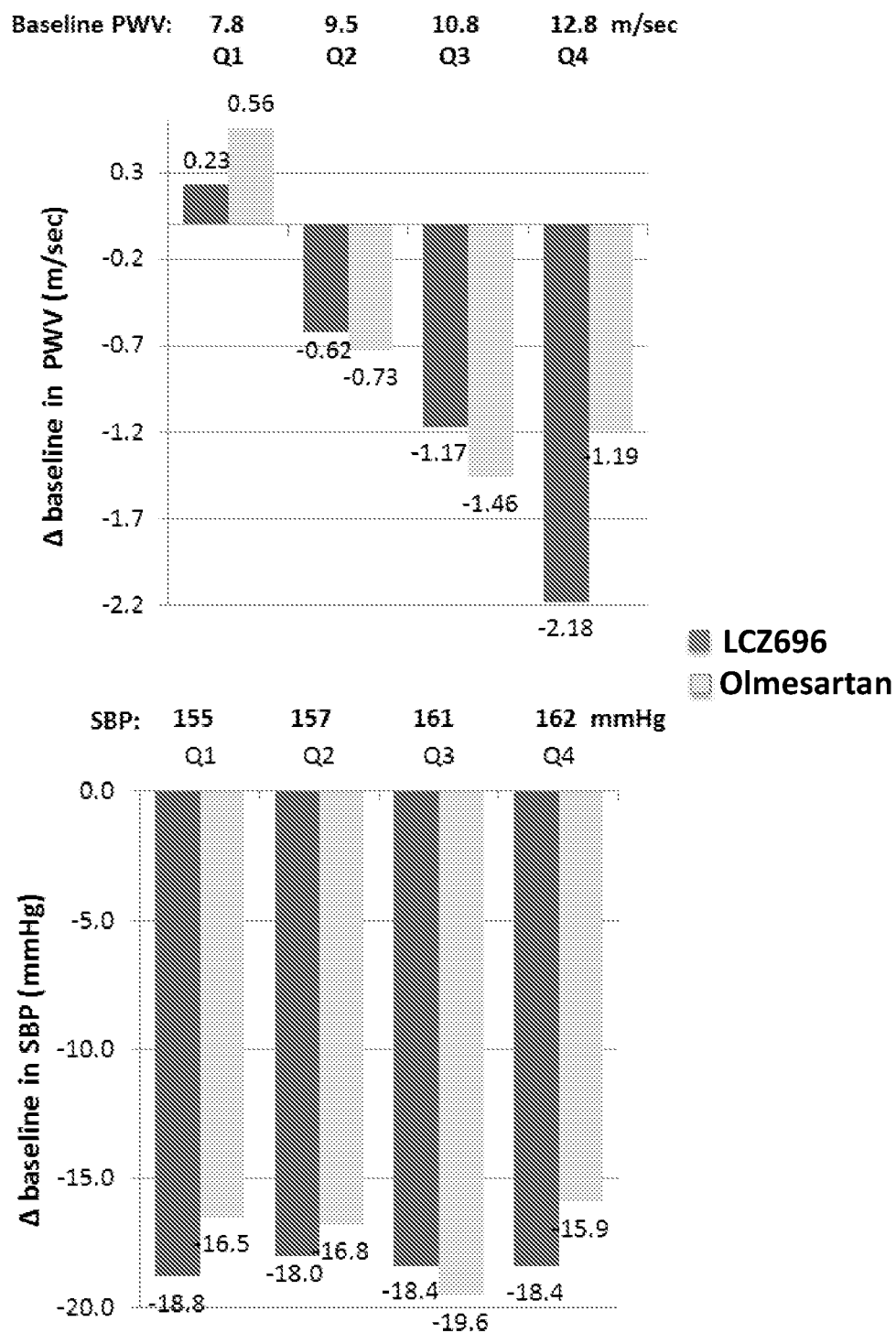
FIG. 4: Change in PWV and brachial SBP at Week 52—PWV Quartile analysis. Notes and abbreviations: PWV quartiles: Q1<8.8 m/s; Q2<10.2 m/s; Q3<11.4 m/s; Q4≥11.4 m/sec; between treatment comparisons utilize paired analysis of patients who had a valid PWV at baseline and Week 52; ANCOVA model included treatment, region, baseline PWV as predictors; PWV, pulse wave velocity; SBP, systolic blood pressure.

FIG. 4 shows the changes in PWV and brachial SBP at Week 52—PWV Quartile analysis. PWV quartiles: Q1<8.8 m/s; Q2<10.2 m/s; Q3<11.4 m/s; Q4≥11.4 m/sec; between treatment comparisons utilize paired analysis of patients who had a valid PWV at baseline and Week 52; ANCOVA model included treatment, region, baseline PWV as predictors; PWV, pulse wave velocity; SBP, systolic blood pressure.

Figure 5:
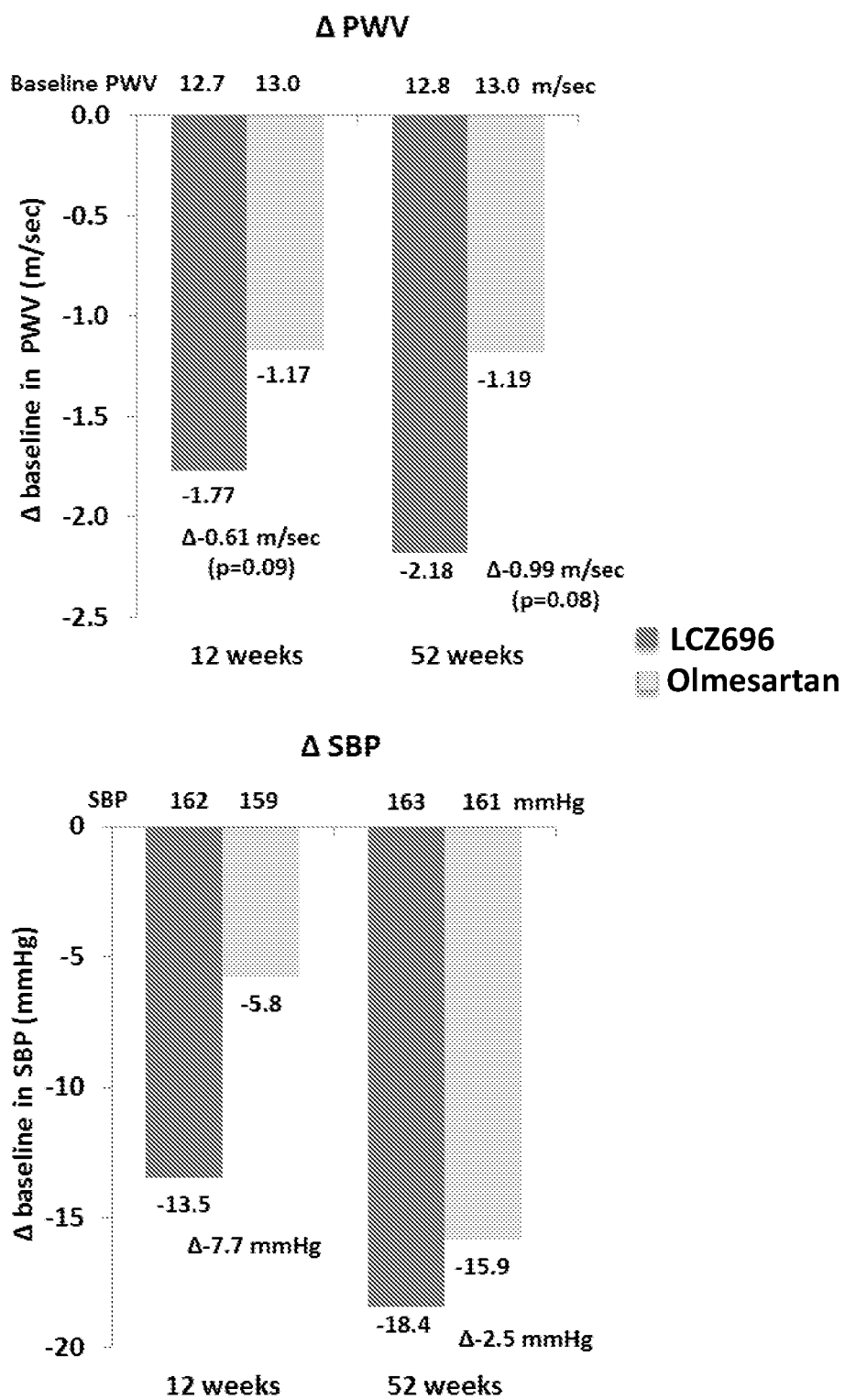
FIG. 5: Upper Quartile changes in PWV and SBP at Week 12 vs. 52. Notes and abbreviations: PWV Q4 quartile: ≥11.4 m/sec; between treatment comparisons utilize paired analysis of patients who had a valid PWV at baseline and Week 52; ANCOVA model included treatment, region, baseline PWV as predictors. PWV, pulse wave velocity; SBP, systolic blood pressure.

FIG. 5 shows the upper Quartile changes in PWV and SBP at Week 12 vs. 52. PWV Q4 quartile: ≥11.4 m/sec; between treatment comparisons utilize paired analysis of patients who had a valid PWV at baseline and Week 52; ANCOVA model included treatment, region, baseline PWV as predictors. PWV, pulse wave velocity; SBP, systolic blood pressure.

| Parameter | Change from baseline to 12 weeks | | | Change from baseline to 52 weeks | | |
|---|---|---|---|---|---|---|
| | LCZ696-regimen | Olmesartan-regimen | Between-treatment difference | LCZ696 regimen | Olmesartan-regimen | Between-treatment difference |
| BP and PP, mmHg | N = 207 | N = 206 | | N = 209 | N = 208 | |
| mscDBP | −6.1 (0.64) | −5.0 (0.6) | −1.1 (0.90) | −8.8 (0.61) | −8.1 (0.61) | −0.7 (0.86) |
| mscMAP | −8.0 (10.75) | −6.7 (11.88) | | −9.6 (12.11) | −9.1 (12.80) | |
| msSBP | −13.3 (15.84) | −9.7 (17.84) | | −17.2 (16.74) | −16.0 (17.53) | |
| msDBP | −5.3 (9.24) | −5.2 (9.96) | | −8.1 (9.32) | −8.5 (9.56) | |
| msPP | −8.0 (11.83) | −4.5 (12.82) | | −9.1 (12.17) | −7.6 (13.04) | |
| | N = 226 | N = 222 | | N = 226 | N = 223 | |
| msMAP | −12.2 (0.68) | −8.6 (0.68) | −3.6 (0.95)* | −13.9 (0.63) | −12.4 (0.64) | −1.5 (0.89) |
| | N = 159 | N = 158 | | N = 169 | N = 173 | |
| macSBP | −12.1 (0.60) | −8.7 (0.60) | −3.4 (0.84)* | −13.0 (0.57) | −13.7 (0.55) | 0.6 (0.79) |
| macDBP | −7.5 (7.55) | −5.8 (8.32) | | −9.0 (7.04) | −9.1 (8.71) | |
| macPP | −4.4 (6.29) | −2.9 (7.61) | | −4.1 (8.11) | −4.6 (7.79) | |
| macMAP | −9.0 (8.55) | −6.75 (9.85) | | −10.33 (8.31) | −10.6 (9.89) | |
| | N = 164 | N = 162 | | N = 174 | N = 176 | |
| maSBP | −13.2 (0.62) | −9.1 (0.62) | −4.1 (0.87)* | −14.1 (0.59) | −14.3 (0.58) | 0.2 (0.82) |
| maDBP | −7.4 (0.37) | −5.5 (0.36) | −2.0 (0.51)* | −8.8 (0.35) | −8.4 (0.34) | −0.4 (0.48) |
| maPP | −5.8 (0.35) | −3.7 (0.35) | −2.1 (0.49)* | −5.3 (0.36) | −5.9 (0.35) | 0.6 (0.50) |
| maMAP | −10.0 (9.26) | −7.1 (10.36) | | −11.2 (9.06) | −11.1 (10.57) | |
| PWV$ | −0.7 (0.12) | −0.6 (0.12) | −0.1 (0.17)* | −0.8 (0.13) | −0.8 (0.13) | −0.1 (0.18) |

Data are mean ± SD unless until specified;
*$P < 0.001$ for LCZ696 vs. olmesartan;
$ n = 192 for LCZ696, n = 196 for olmesartan at Week 12 endpoint; n = 199 for both the treatments at week 52 endpoint;
† n = 207 for LCZ696, n = 206 for olmesartan at Week 12 endpoint; n = 209 for LCZ696, n = 208 for olmesartan at Week 52 endpoint;
‡ n = 159 for LCZ696, n = 158 for olmesartan at Week 12 endpoint; n = 169 for LCZ696, n = 173 for olmesartan at Week 52 endpoint;
AIx, augmentation index;
BP, blood pressure;
CPP, central pulse pressure;
CMAP, central mean arterial pressure;
CASP, central aortic systolic pressure;
DBP, diastolic BP;
eGFR, estimated glomerular filtration rate;
PWV, pulse wave velocity;
PP, pulse pressure;
ma, mean ambulatory;
MAP, mean arterial pressure;
ms, mean sitting;
msc, mean sitting central;
PPA, pulse pressure amplification;
P-C, peripheral minus central

SUMMARY

The study met its primary objective to demonstrate the superiority of LCZ696 400 mg/day to lower CASP and CPP to a greater extent than olmesartan 40 mg/day after 12 weeks of monotherapy.

LCZ696 also lowered 24-hour ambulatory SBP compared to olmesartan after 12-week monotherapy, with more significant BP reduction observed during the night-time period After 52 weeks of therapy and the allowance of open-label add-on antihypertensive medication from Week 12 to control BP, the overall reductions in mean CASP and CPP at Week 52 were numerically greater for the LCZ696 group than the olmesartan group, but the treatment difference did not reach statistical significance. There was no difference between the two regimens in central and brachial BP profiles at Week 52 due to the allowance of add-on antihypertensive therapy; however, a higher percentage of patients in the olmesartan group requiring add-on amlodipine and/or HCTZ.

There was no significant difference in carotid-femoral PWV between the two regimens at both Week 12 and 52, but an ad-hoc analysis of the subgroup of patients with high baseline PWV, showed the LCZ696 regimen tended to reduce PWV to a greater extent than olmesartan regimen at both Week 12 and 52 with the longer-term effect observed despite similar reductions in central and brachial BP.

The study also demonstrated that an LCZ696 regimen was well tolerated with over 80% of patients completed the 52-week study for both treatment groups. The percentage of patients who discontinued the study was balanced between the LCZ696 (19.7%) and olmesartan (18.7%) treatment groups. The percentage of patients who discontinued the study due to an AE was also similar between the LCZ696 (6.6%) and the olmesartan (5.3%) treatment groups.

The percentage of patients with AEs or SAEs was largely comparable between the LCZ696 (57.6% and 7.0%, respectively) and the olmesartan (53.8% and 5.8%, respectively). Three deaths were reported (n=1 with LCZ696 and n=2 with olmesartan). LCZ696 has previously shown efficacy in lowering systolic BP and PP in elderly hypertensive patients. In the study of an elderly patient population with systolic hypertension and widened baseline PP indicative of aortic stiffing, LCZ696 for the first time demonstrated effective lowering of central aortic BP and PP. These results suggest that LCZ696 provides beneficial effect on central hemodynamics in elderly hypertensive patients.

CONCLUSION

The PARAMETER study was the first randomized study demonstrating the ability of LCZ696 to reduce central BP and PP, more effectively than an ARB, in high-risk older patients with systolic hypertension and an increased pulse pressure.

In those patients with the stiffest arteries, the LCZ696 regimen also tended to reduce PWV to a greater extent than an ARB.

These results suggest that LCZ696 provides beneficial effects on central aortic hemodynamics and function, that could provide a therapeutic advantage beyond those observed with RAS blockade alone.

The invention claimed is:

1. A method of reducing arterial stiffness in a human patient showing increased pulse wave velocity (PWV) of more than 12 msec and increased pulse pressure (PP) defined as a wide brachial pulse pressure of more than 60 mm Hg comprising administering to said patient a therapeutically effective amount or a prophylactically effective amount of a combination of sacubitril and valsartan in a 1:1 molar ratio, wherein said patient is aged 60 years or older.

2. The method according to claim 1, wherein the method is for treating, preventing or reducing the risk of experiencing a disorder or disease selected from cognitive impairment, a cardiovascular event, a cerebrovascular event and combinations thereof.

3. The method according to claim 2, wherein said cognitive impairment is selected from the group consisting of mild cognitive impairment, age related cognitive function decline, and Alzheimer's disease.

4. The method according to claim 2, wherein said cardiovascular event is selected from the group consisting of cardiovascular death, myocardial infarction (MI), atrial fibrillation, hospitalization for unstable angina, acute coronary syndrome, other non-coronary ischemic event (transient ischemic attack or limb ischemia), any revascularization procedure (coronary and non-coronary), hospitalization or prolongation of hospitalization for heart failure, and coronary revascularization procedures.

5. The method according to claim 2, wherein said cerebrovascular event is stroke.

6. The method according to claim 1, wherein increased pulse pressure (PP) is defined as a wide brachial pulse pressure of more than 65 mm Hg.

7. The method according to claim 1, wherein increased pulse pressure (PP) is defined as a wide brachial pulse pressure of more than 70 mm Hg.

8. The method according to claim 1, wherein said patient also has an increased central aortic pulse pressure (CPP) defined as a CPP of more than 50 mm Hg.

9. The method according to claim 8, wherein increased central aortic pulse pressure (CPP) is defined as a CPP of more than 55 mm Hg.

10. The method according to claim 8, wherein increased central aortic pulse pressure (CPP) is defined as a CPP of more than 60 mm Hg.

11. The method according claim 1, wherein said patient has a diagnosis of essential hypertension.

12. The method according claim 11, wherein said patient has a mean sitting systolic blood pressure (msSBP) of ≥150 and <180 mm Hg.

13. The method according claim 1, wherein the therapeutically effective amount or the prophylactically effective amount of a combination of sacubitril and valsartan in a 1:1 molar ratio comprises a daily overall dose of the combination of sacubitril and valsartan in a 1:1 molar ratio from about 50 mg to about 1000 mg.

14. The method according to claim 13, wherein the combination of sacubitril and valsartan in a 1:1 molar ratio is administered to the patient once or twice daily with an individual dose of 50 mg, 100 mg, or 200 mg.

15. The method according to claim 14, wherein
  a) the 50 mg dose of sacubitril and valsartan in a 1:1 molar ratio corresponds to 24 mg sacubitril and 26 mg valsartan,
  b) the 100 mg dose of sacubitril and valsartan in a 1:1 molar ratio corresponds to 49 mg sacubitril and 51 mg valsartan, and
  c) the 200 mg dose of sacubitril and valsartan in a 1:1 molar ratio corresponds to 97 mg sacubitril and 103 mg valsartan.

16. The method according to claim 1, wherein the combination of sacubitril and valsartan in a 1:1 molar ratio is delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate (LCZ696).

17. The method according to claim 16, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)buty rate] hemipentahydrate (LCZ696), and wherein
  a) the 50 mg dose of sacubitril and valsartan in a 1:1 molar ratio corresponds to around 56.6 mg LCZ696,
  b) the 100 mg dose of sacubitril and valsartan in a 1:1 molar ratio corresponds to around 113.1 mg LCZ696, and
  c) the 200 mg dose of sacubitril and valsartan in a 1:1 molar ratio corresponds to around 226.2 mg LCZ696.

18. The method according to claim 1, wherein said patient is concomitantly receiving standard of care treatment for preventing or reducing risk of experiencing recurrent cardiovascular events.

19. The method according to claim 18, wherein said standard of care treatment comprises treatment with a stable dose of a beta-blocker, an aldosterone antagonist, and/or a diuretic.

20. The method according to claim 18, wherein said standard of care treatment comprises treatment with a stable dose of a beta-blocker and optionally an aldosterone antagonist.

* * * * *